(12) United States Patent
Barias et al.

(10) Patent No.: US 12,162,814 B2
(45) Date of Patent: Dec. 10, 2024

(54) DIMERIZATION AND TRIMERIZATION OF C5 OLEFINS VIA CATALYTIC DISTILLATION

(71) Applicant: LUMMUS TECHNOLOGY LLC, Bloomfield, NJ (US)

(72) Inventors: Rosette Barias, Spring, TX (US); Michael Jon Scott, Houston, TX (US); Liang Chen, Houston, TX (US)

(73) Assignee: LUMMUS TECHNOLOGY LLC, Houston, TX (US)

( * ) Notice: Subject to any disclaimer, the term of this patent is extended or adjusted under 35 U.S.C. 154(b) by 477 days.

(21) Appl. No.: 17/452,699

(22) Filed: Oct. 28, 2021

(65) Prior Publication Data

US 2022/0127208 A1  Apr. 28, 2022

Related U.S. Application Data

(60) Provisional application No. 63/106,769, filed on Oct. 28, 2020.

(51) Int. Cl.
  *C07C 5/05* (2006.01)
  *B01D 3/00* (2006.01)
  (Continued)

(52) U.S. Cl.
  CPC ............ *C07C 2/26* (2013.01); *B01D 3/009* (2013.01); *B01J 8/0278* (2013.01); *B01J 8/26* (2013.01);
  (Continued)

(58) Field of Classification Search
  None
  See application file for complete search history.

(56) References Cited

U.S. PATENT DOCUMENTS 3,960,978 A  6/1976 Givens et al.
4,021,502 A  5/1977 Plank et al.
(Continued)

FOREIGN PATENT DOCUMENTS

| CN | 1348941 A | 5/2002 |
|---|---|---|
| KR | 101577487 B1 | 12/2015 |
| WO | 2020092774 A1 | 5/2020 |

OTHER PUBLICATIONS

International Search Report issued in Application PCT/US2021/057056, mailed on Feb. 18, 2022 (4 pages).
(Continued)

*Primary Examiner* — Rosalynd A Keys
(74) *Attorney, Agent, or Firm* — Osha Bergman Watanabe & Burton LLP

(57) ABSTRACT

A process for the selective dimerization and etherification of isoolefins. The process including feeding a mixed C5 stream to a selective hydrogenation unit to convert dienes to olefins and isoolefins, producing a hydrogenated effluent stream. The hydrogenated effluent stream is fed to a first fixed bed reactor, producing a first reactor effluent. The first reactor effluent is fed to a catalytic distillation reactor system, producing a first overheads including unreacted olefins, isoolefins, oxygenate, and one or more C5 ethers and a first bottoms including dimers of the isoolefins, any produced trimers of the isoolefins, and heavy oxygenates. The first overheads is fed to a second fixed bed reactor, producing a second reactor effluent including dimers of the isoolefins, unreacted C5s, and unreacted oxygenates. The first bottoms stream and the second reactor effluent are combined and fed to a product splitter, producing a second overheads stream including unreacted C5 olefins, isoolefins, and oxygenates and a second bottoms stream including C10+ hydrocarbons.

18 Claims, 3 Drawing Sheets

(51) Int. Cl.
*B01J 8/02* (2006.01)
*B01J 8/26* (2006.01)
*C07C 2/26* (2006.01)
*C07C 2/28* (2006.01)
*C07C 5/03* (2006.01)
*C07C 41/05* (2006.01)
*C07C 41/06* (2006.01)

(52) U.S. Cl.
CPC .................. *C07C 2/28* (2013.01); *C07C 5/03* (2013.01); *C07C 5/05* (2013.01); *C07C 41/05* (2013.01); *C07C 41/06* (2013.01); *C07C 2531/025* (2013.01)

(56) References Cited

U.S. PATENT DOCUMENTS

| | | | |
|---|---|---|---|
| 4,100,220 A | 7/1978 | Bowman et al. | |
| 4,232,177 A | 11/1980 | Smith, Jr. | |
| 4,242,530 A | 12/1980 | Smith, Jr. | |
| 4,307,254 A | 12/1981 | Smith, Jr. | |
| 4,331,824 A | 5/1982 | Ikeda et al. | |
| 4,336,407 A | 6/1982 | Smith, Jr. | |
| 4,375,576 A | 3/1983 | Smith, Jr. | |
| 4,504,687 A | 3/1985 | Jones, Jr. | |
| 4,551,567 A | 11/1985 | Smith, Jr. | |
| 4,629,710 A | 12/1986 | Smith, Jr. | |
| 4,950,803 A | 8/1990 | Smith, Jr. et al. | |
| 4,987,807 A | 1/1991 | Simon | |
| 5,003,124 A | 3/1991 | Smith, Jr. et al. | |
| 5,118,873 A | 6/1992 | Smith, Jr. | |
| 5,243,102 A * | 9/1993 | Marker | B01D 3/009 568/697 |
| 5,672,795 A | 9/1997 | Vora et al. | |
| 5,792,891 A * | 8/1998 | Adams | C07C 41/06 585/614 |
| 5,877,372 A | 3/1999 | Evans et al. | |
| 6,335,473 B1 | 1/2002 | Bakshi et al. | |
| 6,376,731 B1 | 4/2002 | Evans et al. | |
| 6,689,927 B1 | 2/2004 | Frame et al. | |
| 6,774,275 B2 | 8/2004 | Smith, Jr. et al. | |
| 6,858,770 B2 | 2/2005 | Smith, Jr. et al. | |
| 6,936,742 B2 | 8/2005 | Smith, Jr. | |
| 6,995,296 B2 | 2/2006 | Smith, Jr. et al. | |
| 7,145,049 B2 | 12/2006 | Loescher et al. | |
| 7,250,542 B2 | 7/2007 | Smith, Jr. et al. | |
| 7,288,693 B2 | 10/2007 | Smith, Jr. et al. | |
| 7,319,180 B2 | 1/2008 | Smith, Jr. et al. | |
| 2004/0006252 A1 | 1/2004 | Smith | |
| 2004/0210093 A1 | 10/2004 | Groten et al. | |
| 2006/0030741 A1 | 2/2006 | Smith et al. | |
| 2007/0161843 A1 | 7/2007 | Smith et al. | |
| 2008/0045763 A1 | 2/2008 | Cross et al. | |
| 2008/0064911 A1 | 3/2008 | Loescher et al. | |
| 2019/0232249 A1 | 8/2019 | Xu et al. | |

OTHER PUBLICATIONS

Written Opinion issued in Application PCT/US2021/057056, mailed on Feb. 18, 2022 (5 pages).

* cited by examiner

DIMERIZATION AND TRIMERIZATION OF C5 OLEFINS VIA CATALYTIC DISTILLATION

FIELD OF THE DISCLOSURE

Embodiments disclosed herein relate generally to a process for the dimerization of isoolefins. Some embodiments herein relate to processes and apparatus for the dimerization of isoolefins, such as $C_5$s, at high selectivity. Other embodiments herein relate to processes and apparatus for the concurrent selective dimerization and trimerization of isoolefins, such as $C_5$s, to form a light naphtha cut. Other embodiments herein relate to processes and apparatus for the selective dimerization and trimerization of $C_5$s via catalytic distillation.

BACKGROUND

In order to meet the fuel blending requirements, such as octane rating or vapor pressure requirements, smaller olefin molecules may be upgraded to produce longer chain molecules. Alternatively, the smaller olefin molecules may be etherified to increase the oxygen content of the molecule and the resulting fuel blend. The etherification side reaction may also serve as a moderator reaction to control the main reactor, selectively forming dimers as opposed to trimers and heavier oligomers.

One commonly used method of upgrading smaller olefin molecules, such as $C_2$ to $C_5$ olefins, is a dimerization reaction. Isoamylenes, such as 2-methyl-1-butene and 2-methyl-2-butene, and pentenes, such as 1-pentene and 2-pentene, are commercially significant in many applications. For example, isoamylenes can be one of the comonomers for polymers. These $C_5$s can also be dimerized to produce compounds that can be used as chemical feedstock for further reacting or in gasoline blending or for other petrochemical applications.

Dimerization reactions involve contacting an olefin with a catalyst in order to produce a longer chain molecule. A dimer can consist of two or more constituent olefin molecules. For example, dimerization is a type of oligomerization reaction that is limited to a combination of only two olefin molecules. If the olefin feed contains only one type of olefin, a dimer product is formed. If the olefin feed contains two or more different olefins or olefin isomers, a codimer product may also be formed.

Specifically, $C_4$ olefin dimerization is widely used for producing isooctene, an intermediate that can be hydrogenated to produce isooctane, a high-value gasoline blending additive. Several representative olefin dimerization reactions are shown below:

A gas phase olefin dimerization process is disclosed in U.S. Pat. Nos. 3,960,978 and 4,021,502, where $C_2$ to $C_5$ olefins, fed as pure olefins or in admixture with paraffins, are dimerized via contact with a zeolite fixed catalyst bed. Other dimerization processes are disclosed in, for example, U.S. Pat. Nos. 4,242,530, 4,375,576, 5,003,124, 7,145,049, 6,335,473, 6,774,275, 6,858,770, 6,936,742, 6,995,296, 7,250,542, 7,288,693, 7,319,180, 6,689,927, 6,376,731, 5,877,372, 4,331,824, 4,100,220 and U.S. Patent Application Publication Nos. 20080064911, 20080045763, 20070161843, 20060030741, 20040210093, and 20040006252, among others. Acid resin catalysts have also found use in various other petrochemical processes, including formation of ethers, hydration of olefins, esterifications, and expoxidations, such as described in U.S. Pat. Nos. 4,551,567 and 4,629,710.

Processes for dimerization of olefins over such resin catalysts require periodic shutdowns of the dimerization unit to replace and/or regenerate the catalysts. Further, such solid-catalyzed processes may require additives ("reaction moderators") to promote the selectivity of the catalyst to the dimer, where the additives may result in unwanted acid throw, deactivating the catalyst, and may additionally require complicated separation processes to remove the additive from the resulting product streams.

In any type of dimerization reaction, the dimerization catalyst activity can be drastically reduced due to poisoning, fouling, and coking frequently caused by impurities present in the olefin feed stream. Furthermore, various additives and impurities that may be present in the olefin feed can participate in side reactions leading to formation of undesirable byproducts.

Dimerization reaction additives, such as a reaction moderator, can also participate in undesirable side reactions with the olefin or with the dimerization product. Moderator is frequently added to the dimerization reaction in order to increase the dimer selectivity by limiting the extent of oligomerization reaction to the dimer stage. Suitable moderators include oxygenates, such as water, primary, secondary and tertiary C1-C5 alcohols and ethers. However, as a trade-off to achieving high dimer selectivity, a portion of the moderator can react with an olefin or a dimerization product to form heavy oxygenates, for example, tertiary amyl methyl ether (TAME) from reaction with methanol or tertiary amyl ethyl ether (TAEE) from reaction with ethanol.

Regarding etherification, the reaction of an alcohol and an olefin and concurrent separation of the reactants from the reaction products by fractional distillation has been practiced for some time. The process is variously described in U.S. Pat. Nos. 4,232,177; 4,307,254; 4,336,407; 4,504,687; 4,987,807; and 5,118,873.

Briefly, the alcohol and isoolefin are fed to a distillation column reactor having a distillation reaction zone containing a suitable catalyst, such as an acid cation exchange resin, in the form of catalytic distillation structure, and having a distillation zone containing inert distillation structure. As embodied in the etherification of isobutylene and/or isoamylene, the olefin and an excess of methanol are first fed to a fixed bed reactor wherein most of the olefin is reacted to form the corresponding ether, methyl tertiary butyl ether (MTBE) or tertiary amyl methyl ether (TAME). The fixed bed reactor is operated at a given pressure such that the reaction mixture is at the boiling point, thereby removing the exothermic heat of reaction by vaporization of the mixture. The fixed bed reactor and process are described more completely in U.S. Pat. No. 4,950,803 which is hereby incorporated by reference.

The effluent from the fixed bed reactor is then fed to the distillation column reactor wherein the remainder of the isobutylene or isoamylene are usually converted to the ether and the methanol is separated from the ether which is withdrawn as bottoms. The $C_4$ or $C_5$ olefin stream generally contains only about 10 to 60 percent olefin, the remainder being inerts, which are removed in the overheads from the distillation column reactor.

In some cases, the distillation column reactor may be operated such that complete reaction of the isoolefin is not achieved for a particular reason and therefore there may be significant isoolefin in the overheads, that is, from 1 to 15 wt %, along with unreacted methanol.

Accordingly, there exists a continuing need for improved isoolefin dimerization catalysts, systems, and processes and isoolefin etherification catalysts, systems, and processes.

SUMMARY OF THE DISCLOSURE

According to one or more embodiments disclosed herein is a process for the selective dimerization and etherification of isoolefins. The process may include feeding a mixed $C_5$ stream, comprising isoolefins, olefins, and dienes to a selective hydrogenation unit to convert the dienes to olefins, isoolefins, and some paraffins producing a hydrogenated effluent stream; feeding the hydrogenated effluent stream and a moderator to a first fixed bed reactor containing a first catalyst, producing a first reactor effluent comprising dimers of the isoolefin, unreacted C5s, and oxygenates and unreacted moderator; feeding the first reactor effluent to a catalytic distillation reactor system containing a second catalyst, the second catalyst being configured for both etherification and dimerization, or dimerization only, of isoolefins, producing a first overheads comprising unreacted olefins, isoolefins, oxygenates, and one or more C5 ethers and a first bottoms comprising dimers of the isoolefins, any produced trimers of the isoolefins, and heavy oxygenates; feeding the first overheads to a second fixed bed reactor containing a third catalyst, the third catalyst being the same or different as the first catalyst, producing a second reactor effluent comprising dimers of the isoolefins, unreacted C5s, and unreacted oxygenates; combining the first bottoms stream and the second reactor effluent, forming a combined feed stream; feeding the combined feed stream to a product splitter, producing a second overheads stream comprising unreacted C5 olefins, isoolefins, and oxygenates, and a second bottoms comprising the dimers of the isoolefins and any produced trimers of the isoolefins.

According to one or more embodiments disclosed herein is a process for the flexible production of either dimers or ethers. The process may include feeding a mixed C5 stream, comprising isoolefins, olefins, and dienes to a selective hydrogenation unit to convert the dienes to olefins and isoolefins, producing a hydrogenated effluent stream; feeding the hydrogenated effluent stream and a moderator to a first fixed bed reactor containing a first catalyst which may be configured for dimerization only, producing a first reactor effluent comprising dimers of the isoolefin, unreacted C5s, and oxygenates and unreacted moderator; feeding the first reactor effluent to a catalytic distillation reactor system containing a second catalyst, the second catalyst being configured for both etherification and dimerization, or dimerization only, of isoolefins, producing a first overheads comprising unreacted olefins, isoolefins and oxygenates and a first bottoms comprising dimers of the isoolefins, any produced trimers of the isoolefins, and heavy oxygenates; feeding the first bottoms to a product splitter, producing a second overheads stream comprising un reacted C5 olefins, isoolefins, and oxygenates, and a second bottoms comprising the dimers of the isoolefins and any produced trimers of the isoolefins.

According to one or more embodiments disclosed herein is a system for the flexible production of either dimers or ethers. The system may include a selective hydrogenation unit configured for reacting dienes in a mixed C5 stream, comprising olefins, dienes, and isoolefins, producing a partially hydrogenated feedstream; a first fixed bed reactor containing a first catalyst which may be configured for reacting the partially hydrogenated feedstream and a moderator, producing a first reactor effluent comprising dimers of the isoolefin, unreacted C5s, and oxygenates and unreacted moderator; a catalytic distillate reactor system containing a second catalyst configured for reacting the unreacted C5s in the presence of the second catalyst to form additional dimers of the isoolefin and/or ethers, and producing a first overheads comprising unreacted olefins, isoolefins, and oxygenates and a first bottoms comprising dimers of the isoolefins, any produced trimers of the isoolefins, and heavy oxygenates; a second fixed bed reactor containing a third catalyst configured for reacting the first overheads and producing a second reactor effluent comprising dimers of the isoolefin, unreacted C5s, and unreacted oxygenates; a product splitter configured for separating the second reactor effluent and producing a second overheads stream comprising unreacted C5 olefins, isoolefins, and oxygenates, and a second bottoms comprising the dimers of the isoolefins and any produced trimers of the isoolefins.

Other aspects and advantages will be apparent from the following description and the appended claims.

DETAILED DESCRIPTION

Figure 1:
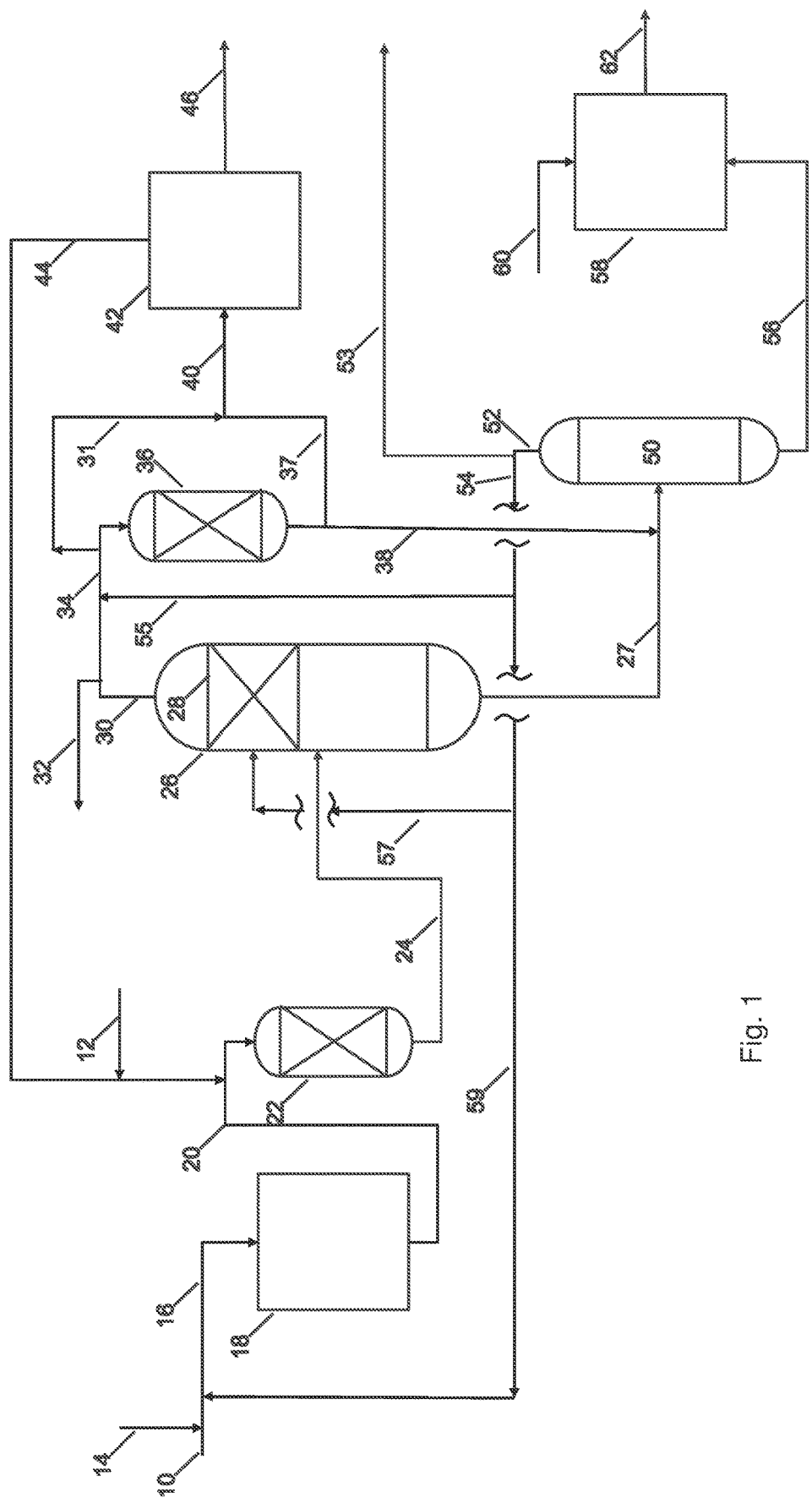
FIG. 1 is a simplified process flow diagram of a system for dimerization and/or trimerization of isoolefins according to embodiments herein.

Embodiments herein relate generally to dimerization and/or etherification of isoolefins.

As used in embodiments disclosed herein, "catalytic distillation reactor system" refers to a system for concurrently reacting compounds and separating the reactants and the products using fractional distillation. In some embodiments, the catalytic distillation reactor system may comprise a conventional catalytic distillation column reactor, where the reaction and distillation are concurrently taking place at boiling point conditions. In other embodiments, the catalytic distillation reactor system may comprise a distillation column combined with at least one side reactor, where the side reactor may be operated as a liquid phase reactor or a boiling point reactor. While both catalytic distillation reactor systems described may be preferred over conventional liquid phase reaction followed by separations, a catalytic distillation column reactor may have the advantages of decreased piece count, reduced capital cost, increased catalyst productivity per pound of catalyst, efficient heat removal (heat of reaction may be absorbed into the heat of vaporization of the mixture), and a potential for shifting equilibrium. Divided wall distillation columns, where at least one section of the divided wall column contains a catalytic distillation structure, may also be used, and are considered "catalytic distillation reactor systems" herein.

The hydrocarbon feed to the reactor(s) may include purified isoolefin streams, such as a feed stream containing primarily isoamylenes, or mixtures of isoamylenes with other C5 olefins and/or paraffins. In other embodiments, hydrocarbon feeds may include a $C_5$ light naphtha cut. When present in mixtures, the tertiary olefins, including isoamylenes such as 2-methyl-2-butene and 2-methyl-1-butene, are more reactive than the normal olefin isomers and are preferentially reacted (dimerized or trimerized). The isoalkanes in the $C_5$ light naphtha cuts may include isobutane, isopentane or mixtures thereof, cyclopentadiene, as well as n-pentane, each of which may act as a diluent in the reactors.

In some embodiments, a C5-containing hydrocarbon stream, such as a C5 naphtha cut, may be fed to a selective hydrogenation unit so that any dienes in the C5 naphtha cut may be converted to 1-pentene, 2-pentene, or isoamylenes, thus allowing for increased dimerization of the isoamylenes. In some embodiments, the 1-petene and 2-pentene may undergo skeletal isomerization to produce additional isoamylene. The resulting selectively hydrogenated stream, including 1-pentene, 2-pentene, or isoamylenes, may be lean in dienes. For example, depending upon the severity of the hydrogenation conditions used, the selectively hydrogenated stream may contain less than 1 weight percent total of dienes; less than 0.5 weight percent total in other embodiments; less than 0.1 weight percent total in other embodiments; and less than 500 ppm total in yet other embodiments.

The C5 isoolefins may be processed according to embodiments herein to selectively dimerize the isoolefins, etherify the isoolefins, or both. In some embodiments, the C5 isoolefins may undergo some trimerization. In such embodiments, the trimerization reaction may be moderated by one or more oxygenate moderators. Systems according to embodiments herein may be used to flexibly produce dimers during a production campaign, and when market demands change, to produce ethers during a production campaign. Catalysts used in reactors and distillation column reactors according to embodiments herein may have functionality to selectively dimerize isoolefins as well as to etherify the isoolefins. Accordingly, the process may be transitioned between dimerization and etherification readily, without the need to change catalysts. Rather, operating conditions, including temperature, pressure, residence time, and reactant concentrations, among others, may be transitioned appropriately to effect the desired reaction.

Processes disclosed herein may include any number of reactors, including catalytic distillation reactor systems, both up-flow and down-flow. Use of catalytic distillation reactor systems may prevent foulants and heavy catalyst poisons in the feed from building up within the reaction zone(s). In addition, clean reflux may continuously wash the catalytic distillation structure in the reaction zone. These factors combine to provide a long catalyst life. The heat of reaction evaporates liquid and the resulting vapor is condensed in the overhead condenser to provide additional reflux. The resulting temperature profile in the reaction zone in the catalytic distillation reaction system is much closer to an isothermal catalyst bed rather than the adiabatic temperature increase typical of conventional fixed bed reactors.

Other reactors useful in embodiments disclosed herein may include traditional fixed bed reactors, boiling point reactors, and pulsed flow reactors, where the reactant flow and product flow may be co-current or counter-current. Boiling point and pulsed flow reactors may also provide for a continuous washing of the catalyst in addition to capturing at least a portion of the heat of reaction through evaporation, allowing for an improved reactor temperature profile as compared to conventional fixed bed reactors. Reactors useful in embodiments disclosed herein may be used as a stand-alone reactor or may be used in combination with one or more reactors of the same or different type.

Any type of reactor may be used to carry out the reactions described herein. The examples of reactors suitable for carrying out the reactions involving isoolefin reactions according to embodiments herein may include distillation column reactors, divided wall distillation column reactors, traditional tubular fixed bed reactors, bubble column reactors, slurry reactors equipped with or without a distillation column, pulsed flow reactors, catalytic distillation columns wherein slurry solid catalysts flow down the column, or any combination of these reactors. Multiple reactor systems useful in embodiments disclosed herein may include a series of multiple reactors or multiple reactors in parallel for the first reaction zone. A person of ordinary skill in the art would recognize that other types of reactors may also be used.

The reactors useful in embodiments disclosed herein may include any physical devices or a combination of two or more devices, including reactors and reactor systems as described above. The reactor(s) may have various internal devices for vapor-liquid separation and vapor/liquid traffic. Reaction zones within the reactor(s) may include "wettable" structure and/or packing. Wettable structure and packing useful in embodiments disclosed herein may include various distillation structures and packing materials, which may be catalytic or non-catalytic. Suitable wettable structure and packing may include, for example, random or dumped distillation packings which are: catalytically inert dumped packings that contain higher void fraction and maintain a relatively large surface area, such as, Berl Saddles (Ceramic), Raschig Rings (Ceramic), Raschig Rings (Steel), Pall rings (Metal), Pall rings (Plastic, e.g. polypropylene) and the like. Monoliths, which are structures containing multiple, independent, vertical channels and may be constructed of various materials such as plastic, ceramic, or metals, in which the channels are typically square, are also suitable wettable structures. Other geometries could also be used.

Other materials that promote the distribution of liquid and vapors may also be used, including mist eliminators, demisters, or other wire or multi-filament type structure. Such multi-filament structures may include one or more of fiberglass, steel, Teflon, polypropylene, polyethylene, polyvinylidenedifluroride (PVDF), polyester, or other various materials, which may be knitted (or co-knit, where more than one type of filament or wire structure is used), woven, non-woven, or any other type of multi-filament structure. Structures including multifilament wires as typically used in demister services, structures including an element of woven fiberglass cloth, and high surface area stainless steel structured packings are preferred.

Compositions and reactant admixtures useful for some embodiments disclosed herein may be in a partial liquid phase in the presence of an acid cation resin catalyst either in straight pass type reaction or in a catalytic distillation reaction where there is both a vapor and liquid phase and a concurrent reaction/fractionation. Catalysts used in dimerization reactors may include acid resins, such as AMBERLYST 15 (available from Rohm and Haas) or related oleum derived resins and may include phosphoric acid derived catalysts, such as those known to the industry as SPA (solid phosphoric acid) catalysts, or other sulfonic acid resins.

Reactors according to embodiments disclosed herein may include one or multiple reaction zones.

One of the primary products from processes according to embodiments herein may include dimers of the isoolefins. For example, isoamylene may be dimerized to form a $C_{10}$ olefin or diisoamylene (DIA). In some embodiments, the dimers have 8 to 10 carbon atoms and correspond to dimers prepared from $C_4$ or $C_5$ olefins. In other embodiments, some amount of the isoamylene may be trimerized to form a $C_{15}$ tertiary olefin.

In prior C5 dimerization schemes, fixed bed reactions are staged to increase the selectivity toward the C10 dimer. The present inventors have found that through proper dimerization reaction conditions and appropriate use of a moderator in each reactor, the need for an intermediate depentanizer may be minimal while still achieving a high isoolefin conversion. Additionally, using one or more oxygenate moderators, the trimerization of the C5 isoolefins may be controlled. Suitable moderators may include water, C1-C5 primary alcohols such as methanol, ethanol, 1-propanol, etc., as well as C1-C5 secondary and tertiary alcohols such as 2-propanol, 2-butanol, tertiary amyl alcohol (TAA), etc., and ethers such as TAME and TAEE. Lighter oxygenates may react with an olefin or a dimerization product to form additional heavy oxygenates, for example, TAME and/or TAEE. In some embodiments, the moderators may include methanol, ethanol, or a combination thereof.

Following reaction in upstream reactors, such as fixed bed reactors, the effluent from the primary fixed bed reactor may be fed to a catalytic distillation column reactor to separate the reaction products while targeting complete conversion of the isoamylene. Embodiments herein contemplate continued dimerization in the catalytic distillation column reactor. Other embodiments herein contemplate etherification in the catalytic distillation column reactor. The catalytic distillation reactor system may be configured to have a single-purpose or dual-purpose catalyst bed, or may be configured to have an upper and a lower catalyst bed where one catalyst bed has a catalyst configured for dimerization and trimerization of isoolefins, and the other catalyst bed has a catalyst configured for etherification of isoolefins. The catalyst beds may be in equal parts, or there may be more or less of one catalyst depending on the desired production of C10+ olefins and/or the amount of moderator available for controlling the trimerization and/or etherification reactions.

The dimerization and trimerization of isoolefins may be carried out in a partial liquid phase in the presence of an acid cation resin catalyst either in straight pass type reaction or in a catalytic distillation reaction where there is both a vapor and liquid phase and a concurrent reaction/fractionation. Catalysts used in dimerization reactors may include acid resins, or related oleum derived resins and may include phosphoric acid derived catalysts, such as those known to the industry as SPA (solid phosphoric acid) catalysts.

Oxygen-containing moderators may be used to influence the selectivity of the dimerization reaction to the dimer product, as opposed to the trimer product, and control the etherification reaction. Oxygen-containing moderators useful in embodiments disclosed herein may include water as well as tertiary alcohols and ethers. For example, the oxygen-containing moderator may include at least one of: water, tertiary butyl alcohol (TBA), methanol, propanol, methyl tertiary butyl ether (MTBE), ethanol, ethyl tertiary butyl ether (ETBE), tertiary amyl ethyl ether (TEAA), and glycerin. In one or more embodiments, the moderator may be MTBE, TBA, methanol or water, or combinations thereof, for the dimerization reaction. In some embodiments, a methanol stream may be fed to the process as an initial moderator. After reaction in a fixed bed reactor and/or catalytic distillation reactor MTBE, TBA, TEAA, or other heavy oxygenates may be generated. These heavy oxygenates may be recycled as the moderator, thereby reducing the amount of fresh methanol needed for the overall process.

Dimerization reactions carried out in the presence of the oxygen-containing moderators may concurrently produce dimers, and some trimers, of the isoolefins, and various oxygen-containing byproducts due to reaction of a moderator with an isoolefin or an isoolefin dimer. For example, the oxygenated dimerization byproducts may include $C_5$-$C_{16}$ ethers and $C_5$-$C_{12}$ alcohols. Isoamylene, for example, may react with methanol (moderator) to form tertiary amyl methyl ether (TAME). In some embodiments, 1-pentene or 2-pentene present may react with a moderator to form secondary ethers, such as secondary amyl methyl ether (SAME), which may be undesireable. Such dimerization process in the presence of a moderator, may eliminate the need for an intermediate deisopentanizer.

The resulting dimers and trimers may be used, for example, as a raw material for the production of various chemicals, such as epoxides, herbicides, pesticides, and for flavors or perfumes. In other embodiments, the dimers and trimers may be fed to an alkylation system, where the dimers and trimers may dissociate into constituent olefins and react with an alkane to produce an alkylate in the gasoline-boiling range. The dimers and trimers may also be hydrogenated to form gasoline-range hydrocarbons, such as iso-decane, and other hydrocarbons, such as isoparaffins for petrochemical applications such as solvents or cosmetics. In yet other embodiments, the dimers and trimers containing stream may be used as a gasoline-range hydrocarbon blendstock without hydrogenation or alkylation.

Operating conditions within catalytic distillation reactor systems for dimerizing isoolefins may include temperatures and pressures sufficient for a) recovery of the unreacted C5 hydrocarbons, water, and other light components as an overhead vapor fraction, b) the desired reactivity of the isoolefins over the catalyst, and c) recovery of the dimer and heavy oxygenates as a bottoms liquid fraction. The temperature within the reaction zone may thus be intimately linked to the pressure, the combination of which provides for boiling of the isoolefin and water within the reaction zone(s). Higher temperatures may be required in portions of the column below the reaction zone, thus providing for the separation of the dimer from the unreacted feed compounds. Depending on the conversion in the primary fixed bed reactor and the catalytic distillation reactor system, a finishing reactor, or secondary fixed bed reactor may further process the isoamylene in the catalytic distillation reactor system overheads, further increasing the conversion of isoamylene to dimers of isoamylene.

Typical conditions for the catalytic distillation TAME reaction include catalyst bed temperatures of about 65-90° C., overhead pressures of about 2.5-5 barg and equivalent liquid hourly space velocities of about 2.0 to 5.0 $hr^{-1}$. The temperature in the column is determined by the boiling point of the liquid mixture present at any given pressure. The temperature in the lower portions of the column will reflect the constitution of the material in that portion of the column, which will be higher than the overhead; that is, at constant pressure a change in the temperature indicates a change in the composition in the column. To change the temperature, the pressure in the column may be changed. Temperature control in the reaction zone is thus controlled by the pressure with the addition of heat (the reactions being exothermic) only causing more boil up. By increasing the pressure the temperature is increased, and vice versa. Even though a distillation column reactor is used, some of the isoolefin may be unconverted and may exits the column with the overheads.

Any ether product formed is removed from the distillation column reactor as a bottoms, along with the dimers, and any formed trimers, in the effluent from the upstream reactors. The overheads may contain unreacted light alcohols, such as methanol or ethanol used as a moderator in the upstream reactors and/or a reactant in the distillation column reactor, and isoolefin along with light inerts, such as normal pentene and pentanes.

Referring now to FIG. 1, a simplified process flow diagram of a system for the dimerization and/or etherification of isoolefins according to embodiments disclosed herein is illustrated.

When operating in dimerization mode, a hydrocarbon feed, such as a raffinate from a pentadiene separation process, comprising isoolefins, such as isoamylene (2M1B and 2M2B), and one or more of isopentane, 1-petene, pentadiene, cyclopentadiene, n-pentane, and 2-pentene, may be fed via a flow line 10, to a selective hydrogenation unit (SHU) 18 suitable for partially hydrogenating the feed. Pentadiene in the feed may be partially, or completely, hydrogenated to form isoamylene and n-pentanes. In some embodiments, the pentadiene in the feedstock may be limited to less than 3000 ppm. Additionally, hydrogen may be fed to SHU 18 via flow line 14.

The partially hydrogenated feed 20, containing isoamylene (2M1B and 2M2B), and one or more of isopentane, 1-petene, n-pentane, 2-pentene, and hydrogen may then be fed to a first fixed bed reactor 22 containing a first catalyst suitable for the dimerization and/or minor etherification of isoamylene. A reaction moderator, such as C1-C5 alcohols or other oxygenates, may also be fed to the first fixed bed reactor 22 via a flow line 12. Alternatively, and/or additionally, oxygenate, such as methanol and/or ethanol or other C1-C5 alcohols, may be fed to the first fixed bed reactor 22 via flow line 44. Such alcohols may come from an upstream oxygenate rectification section.

In reactor 22, the isoamylene reacts in the presence of the catalyst contained in the reaction zone to convert a portion of the isoamylene to dimers of isoamylene such as isodecene, and/or ethers, such as TAME or TAEE.

The effluent 24 from reactor 22 may then be fed to a catalytic distillation reactor system 26, also containing a resin catalyst 28 suitable for dimerization and etherification reactions. While illustrated as a single catalyst bed, resin catalyst 28 may be multiple separate catalyst beds with the same or different catalysts for concurrent dimerization and etherification. In catalytic distillation reactor system 26, the isoamylene reacts in the presence of the catalyst contained in the reaction zone to convert a portion of the isoamlyene to form additional dimers, including dimers of isoamylene such as isodecene, trimers, and/or additional ethers, such as TAME or TAEE, in addition to those produced in reactor 22. Feeding effluent 24 to catalytic distillation reactor system 26 may, in some embodiments, be done without the step of an intermediate depentanizer.

If necessary or desired, additional C1-C5 alcohols (not illustrated) may be fed to catalytic distillation reactor system 26. The feed of the effluent 24 from reactor 22 may be introduced to the catalytic distillation reactor system 26 below the reaction zone containing a catalyst suitable for dimerization and/or etherification reactions. Such catalyst may be the same, or different, from the catalyst in reactor 22. The heavier reaction products, including TAME or TAEE, any formed tertiary amyl alcohol (TAA), dimers of isoamlyene, and any formed trimers of isoamylene, may distill downward, while the unreacted isoamylene and lighter components, including 1-pentene, 2-pentene, n-pentane, and oxygenates, such as DME or DEE, distill upward into the reaction zone, where the isoamlyene reacts in the presence of the catalyst contained in the reaction zone to convert a portion of the isoamylene to additional dimers of isoamylene such as isodecene, and/or ethers, such as TAME or TAEE.

The overhead distillate 30 from catalytic distillation reactor system 26 may include unreacted C5s, such as n-pentane, 2-pentene, and 1-pentene, as well as unreacted methanol and/or ethanol and isoamylene, and may be sent to one or more downstream processes such as alcohol extraction and recovery, alkylation, isomerization, or metathesis processes. In the embodiments where the unreacted stream is sent to isomerization, an isomerized effluent may be recycled to the reactor 22.

In one or more embodiments, the overhead distillate 30 may be partially removed from the process via flow line 32. The portion of the overhead distillate 30 not removed from the system may be fed to a secondary fixed bed reactor 36, via flow line 34, containing a third catalyst suitable for dimerization and/or etherification of isoamylene, or a methanol and/or ethanol recovery system 42 via flow lines 31 and 40. The alcohol recovery system 42 may separate unreacted C1-C5 alcohols, such as methanol and/or ethanol, from the isoamylene, 1-pentene, 2-pentene, n-pentane, and other oxygenates, producing an alcohol recycle stream 44 and a C5 product stream 46. The portion of the overhead distillate 34 which is fed to the second fixed bed reactor 36 may undergo additional dimerization and/or etherification, producing a second effluent stream 38 containing TAME or TAEE, any formed tertiary amyl alcohol (TAA), dimers of isoamlyene, any formed trimers of isoamylene, and unreacted 1-pentene and 2-pentene. If the concentration of dimers and heavier components in the second effluent 38 is low, a portion of the second effluent may be fed via flow 37 and 40 to the alcohol recovery system 42 for additional recovery of C5s and unreacted oxygenates.

The catalytic distillation reactor system bottoms 27 may include dimers, and some trimers, TAME, TAEE, and TAA, and other oxygenates produced via reaction in reactors 24 and 26, may be combined with the second effluent 38 and fed to a C5/C10 product splitter 50. The product splitter 50 may produce a second overheads stream 52 containing one or more C5s, such as 1-pentene, 2-pentene, n-pentane, and unreacted isoamylene, uncreated oxygenates including methanol and/or ethanol, and any produced TAME, TAEE, or TAA. The product splitter 50 may also produce a second bottoms stream 56 containing the dimers and any formed trimers of isoamlylene. The second bottoms stream 56 may be fed to a total hydrogenation unit 58, with a second hydrogen feed 60, to convert the dimers and trimers of isoamylene into C10 and C15 paraffins, producing a C10+ product stream 62. While illustrated with the second bottoms stream 56 being fed to the total hydrogenation unit 58, in some embodiments a dimerized olefin product may be desired. In such embodiments, the second bottoms stream 56 may be taken as a product, and the total hydrogenation unit 58 is not in service.

The second overhead stream 52 may be split into a second product stream 53 and a recycle stream 54. Both the second product stream 53 and recycle stream 54 may have the same composition and include one or more C5s, such as 1-pentene, 2-pentene, n-pentane, and unreacted isoamylene, unreacted oxygenates including methanol and/or ethanol, and any produced TAME, TAEE, or TAA. The recycle stream 54 may be recycled to one or more of the second fixed reactor 36 via flow line 55, catalyst distillation reactor system 26 via flow line 57, and the SHU 18 via flow line 59.

The C5 product stream 46, second product stream 53, and C10+ product stream may be used as a raw material for various downstream processes. For example, these streams may be used as a raw material for the production of various chemicals, such as epoxides, herbicides, pesticides, flavors, perfumes, solvents, or cosmetics. In other embodiments, in gasoline blending.

While generally described above as producing a dimerization product, the system described herein may, in one or more embodiments, be operated in etherification mode to produce a TAME or TAEE product. When the system is used for production of TAME or TAEE by increasing the feed ratio of oxygenates to mixed C5s and not operating the total hydrogenation unit 58.

In one or more embodiments, the process may initially be producing dimers as a targeted product, separating the dimers of the isoolefins from unreacted oxygenates and unreacted C5s in the catalytic distillation reactor system 26, producing a bottoms stream comprising the dimers of the isoolefins, and an overhead stream comprising unreacted light oxygenates and C5s. During a first period of time, the system may be operated in dimerization mode where the oxygenates are fed at a concentration for the oxygenate to be effective as a reaction moderator, producing dimers of the isoolefins. After running in dimerization mode, the amount of oxygenates fed may be increased to a concentration for the oxygenate to be effective as a reactant, thereby producing ethers of the isoolefin. During etherification, the bottoms fraction via a flow line 27 and second effluent via flow line 38 may be taken directly as product. After running the process in etherification mode for an amount of time, the concentration of oxygenates may be reduced and the bottoms fraction via a flow line 27 and second effluent via flow line 38 may be again fed to product splitter 50.

For example, when operating in dimerization mode, the mixed C5s to oxygenates ratio may be from 5:1 to 2:1 with the oxygenates being primarily C1-C5 alcohols, MTBE, ETBE, TAEE, or TAME, and when operating in etherification mode, the mixed C5s to oxygenates ratio may be from 2:1 to 1:2 with the oxygenates being primarily methanol and/or ethanol.

Accordingly, disclosed herein is a system, which may flexibly produce a dimerization product or an etherification product without having to take reactors out of service. The switch from dimerization to etherification may only require the increase in oxygenates feed and, when additional separation of the resulting product is not desired. Both processes may function with suitable high isoamylene conversion without the need for a depentanizer.

While the system is illustrated as including two fixed bed reactors, more or fewer reactors may be used. In such embodiments, the feed of oxygenates, such as C1-C5 alcohols, may be staged so as to achieve the desired selectivity in the dimerization and/or etherification reactions.

Figure 2:
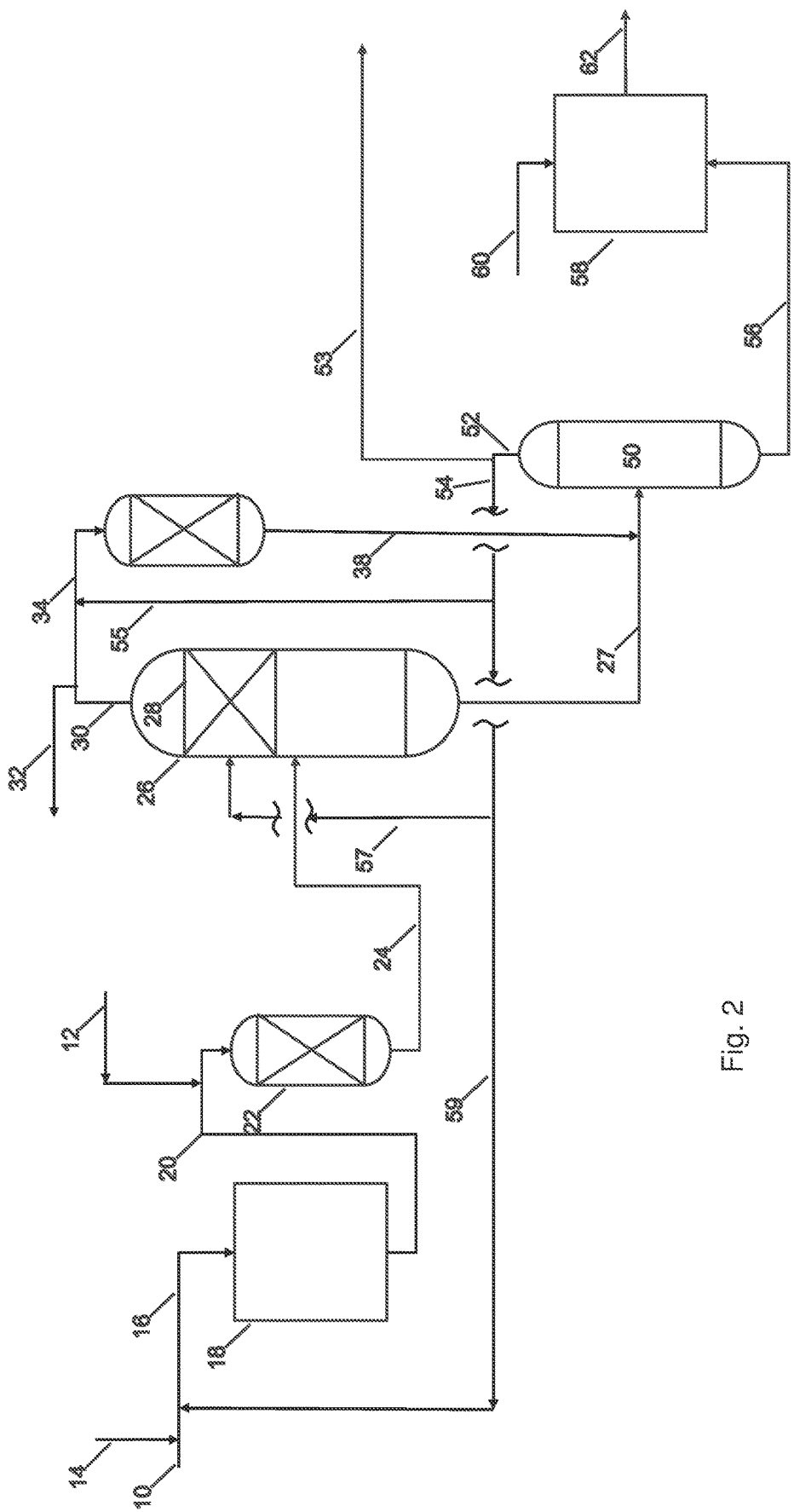
FIG. 2 is a simplified process flow diagram of a system for dimerization and/or trimerization of isoolefins according to embodiments herein.

For example, as illustrated in FIG. 2, in embodiments where the amount of methanol in the first overheads 30 is low, the entirety of the overheads, not removed via flow line 32, may be fed via flow line 34 to the second fix bed reactor. In these embodiments, the alcohol recovery system 42 may not be necessary.

Figure 3:
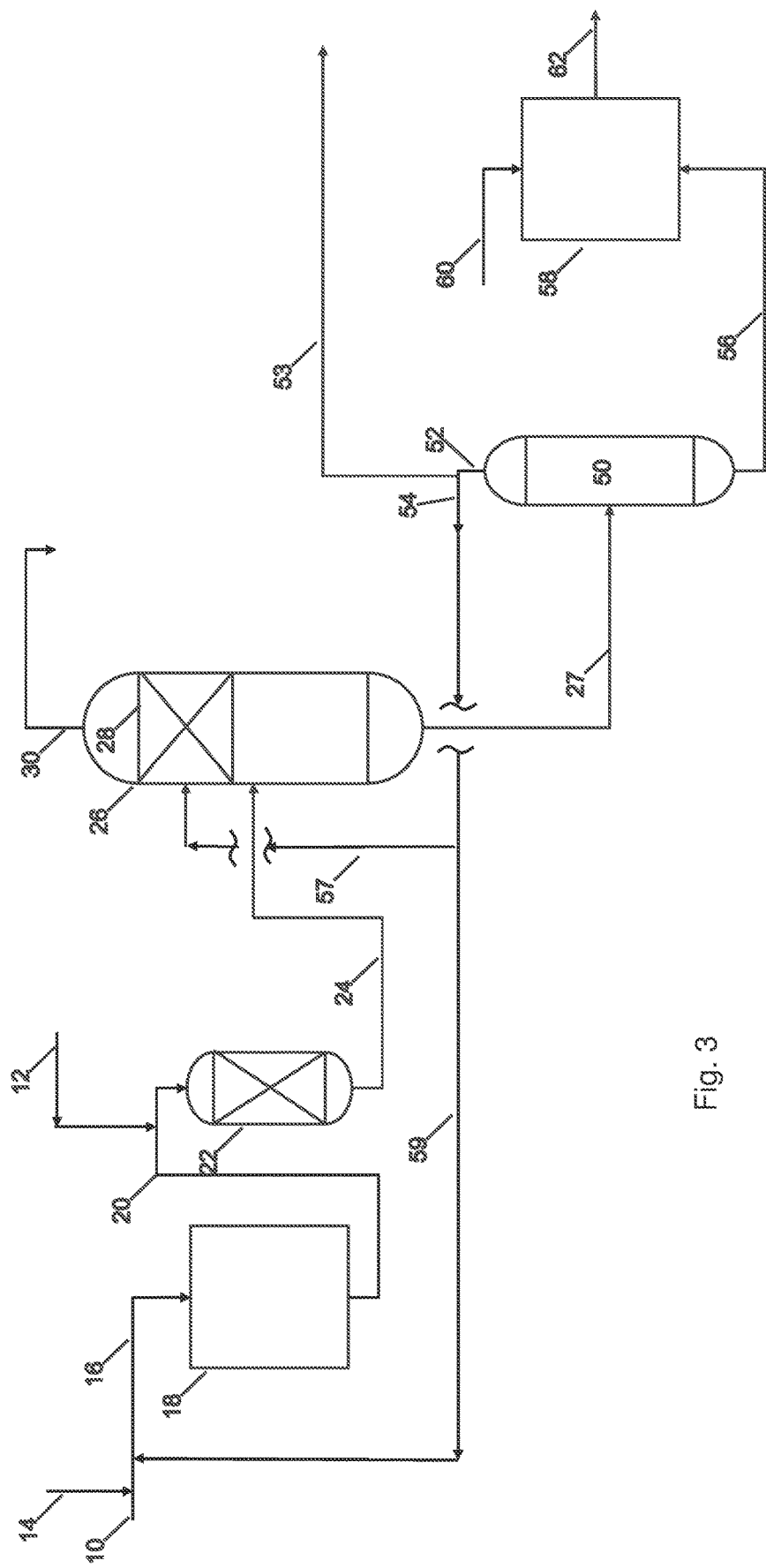
FIG. 3 is a simplified process flow diagram of a system for dimerization and/or trimerization of isoolefins according to embodiments herein.

As illustrated in FIG. 3, in embodiments where the conversion of isomaylene in the first fixed bed reactor 22 and the catalytic distillation reactor system 26 are high, the second fixed bed reactor may be unnecessary, and the bottoms fraction 27 may be the only feed to the product splitter 50.

Additionally, embodiments herein may provide for the flexibility in producing both ethers and/or isoolefins. For example, the system may be used for an extended run to produce TAME or TAEE, and then transitioned to being used for an extended run to produce isoamylene dimers.

As described above, embodiments herein provide for flexible dimerization and/or etherification of isoolefins. In certain embodiments of the present disclosure, isoamylene undergoes a controlled dimerization process in a series reactor configuration in the presence of oxygenates and/or moderators under mild conditions. Additional oxygenates reaction is completed in the subsequent catalytic distillation tower that supplements the requirement of the moderator in the reaction section. The advantages of a series reactor configuration includes higher production of C10 olefins and lower trimers and tetramers formation.

The present disclosure, among other things, provides a reduction in Capex by eliminating the need for a depentanizer between the fixed bed reactors while maximizing the isoamylene concentration and conversion. The removal of isodecene and heavier molecules is not required to achieve high overall isoamylene conversion.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the selective dimerization and etherification of isoolefins, the process comprising:
    feeding a mixed C5 stream, comprising isoolefins, olefins, and dienes to a selective hydrogenation unit to convert the dienes to olefins, isoolefins, and paraffins, producing a hydrogenated effluent stream;
    feeding the hydrogenated effluent stream with a moderator to a first fixed bed reactor containing a first catalyst, producing a first reactor effluent comprising dimers of the isoolefin, unreacted C5s, one or more oxygenates, and unreacted moderator;
    feeding the first reactor effluent to a catalytic distillation reactor system containing a second catalyst, the second catalyst being configured for etherification and/or dimerization of isoolefins, producing a first overheads comprising unreacted olefins, isoolefins, oxygenate, and one or more C5 ethers and a first bottoms comprising dimers of the isoolefins, any produced trimers of the isoolefins, heavy oxygenates and unreacted moderator,
    feeding the first overheads to a second fixed bed reactor containing a third catalyst, the third catalyst being the same or different as the first catalyst, producing a second reactor effluent comprising dimers of the isoolefins, unreacted C5s, the one or more oxygenates and unreacted moderator;
    combining the first bottoms stream and the second reactor effluent, forming a combined feed stream; and
    feeding the combined feed stream to a product splitter, producing a second overheads stream comprising unreacted C5 olefins, isoolefins, moderator, and oxygenates, and a second bottoms comprising the dimers of the isoolefins and any produced trimers of the isoolefins and heavier oligomers.

2. The process of claim 1, further comprising feeding the second bottoms and a hydrogen stream to a total hydrogenation unit, producing a C10+ paraffin product stream.

3. The process of claim 1, wherein the oxygenate comprises C1-C5 alcohols, the process further comprising:
feeding a portion of the first overheads stream to an oxygenate recovery system, producing an oxygenate stream and a C5 hydrocarbon stream;
recycling the oxygenate stream to the first fixed bed reactor as the moderator.

4. The process of claim 1, further comprising recycling a portion of the second overhead stream to the selective hydrogenation unit, the catalytic distillation reactor system, and/or the second fixed reactor.

5. The process of claim 1, wherein the isoolefin is 2-methyl-1-butene and 2-methyl-2-butene, and wherein the oxygenate stream comprises methanol and/or ethanol.

6. The process of claim 1, wherein the oxygenate and/or moderator is fed to the first and second fixed bed reactors at a concentration for the oxygenate to act as a moderator for the dimerization of the isoolefin, and wherein the oxygenate is fed to the catalytic distillation reactor system at a concentration to act as a reactant producing ethers.

7. The process of claim 1, wherein the oxygenate is fed to each of the first and second fixed bed reactors and the catalytic distillation reactor system at a concentration for the oxygenate to act as a moderator for the dimerization of the isoolefin.

8. The process of claim 1, wherein the first, second, and third catalysts are each a catalyst capable of being catalytically active for both dimerization and etherification at respectively appropriate reaction conditions, and wherein the catalyst is a sulfonic acid catalyst.

9. The process of claim 1, further comprising recovering a portion of the second overheads stream as a mixed product stream.

10. A process for the flexible production of dimers and ethers comprising:
feeding a mixed C5 stream, comprising isoolefins, olefins, and dienes to a selective hydrogenation unit to convert the dienes to olefins and isoolefins, producing a hydrogenated effluent stream;
feeding the hydrogenated effluent stream and a moderator to a first fixed bed reactor containing a first catalyst, producing a first reactor effluent comprising dimers of the isoolefin, unreacted C5s, oxygenates, and unreacted moderator;
feeding the first reactor effluent, without componential separation, to a catalytic distillation reactor system containing a second catalyst, the second catalyst being configured for etherification and/or dimerization of isoolefins, producing a first overheads comprising unreacted olefins, isoolefins, oxygenate, and unreacted moderator, and one or more C5 ethers and a first bottoms comprising dimers of the isoolefins, any produced trimers of the isoolefins, heavier oligomers, and heavy oxygenates; and
feeding the first bottoms to a product splitter, producing a second overheads stream comprising unreacted C5 olefins, isoolefins, and oxygenates, and a second bottoms comprising the dimers of the isoolefins and any produced trimers of the isoolefins and heavier oligomers.

11. The process of claim 10, further comprising feeding the second bottoms and a hydrogen stream to a total hydrogenation unit, producing a C10+ paraffin product stream.

12. The process of claim 10, wherein the oxygenate comprises C1-C5 alcohol, the process further comprising:
feeding the first overheads stream to an oxygenate recovery system, producing an oxygenate stream and a C5 hydrocarbon stream;
recycling the oxygenate stream to the first fixed bed reactor as the moderator.

13. The process of claim 10, further comprising recycling a portion of the second overhead stream to the selective hydrogenation unit and/or the catalytic distillation reactor system.

14. The process of claim 10, wherein the isoolefin is 2-methyl-1-butene and 2-methyl-2-butene, and wherein the oxygenate stream comprises methanol and/or ethanol.

15. The process of claim 10, wherein the oxygenate is fed to the first fixed bed reactors at a concentration for the oxygenate to act as a moderator for the dimerization of the isoolefin, and wherein the oxygenate is fed to the catalytic distillation reactor system at a concentration to act as a reactant producing ethers.

16. The process of claim 10, wherein the oxygenate is fed to each of the first fixed bed reactors and the catalytic distillation reactor system at a concentration for the oxygenate to act as a moderator for the dimerization of the isoolefin.

17. The process of claim 10, wherein the first catalyst and second catalyst are each a catalyst capable of being catalytically active for both dimerization and etherification at respectively appropriate reaction conditions, and wherein the catalyst is a sulfonic acid catalyst.

18. The process of claim 10, further comprising recovering a portion of the second overheads stream as a mixed product stream.

* * * * *